United States Patent
Vinluan et al.

(10) Patent No.: US 9,192,462 B2
(45) Date of Patent: Nov. 24, 2015

(54) LOW PROFILE STENT GRAFT AND DELIVERY SYSTEM

(71) Applicant: TriVascular, Inc., Santa Rosa, CA (US)

(72) Inventors: Jenine S. Vinluan, Petaluma, CA (US); Mary Jane Marston, Windsor, CA (US); Mark E. Purter, Windsor, CA (US); Riley King, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 75 days.

(21) Appl. No.: 13/803,037

(22) Filed: Mar. 14, 2013

(65) Prior Publication Data

US 2013/0268057 A1 Oct. 10, 2013

Related U.S. Application Data

(60) Provisional application No. 61/621,038, filed on Apr. 6, 2012.

(51) Int. Cl.
*A61F 2/06* (2013.01)
*A61F 2/07* (2013.01)

(52) U.S. Cl.
CPC ... *A61F 2/06* (2013.01); *A61F 2/07* (2013.01); *A61F 2002/075* (2013.01); *Y10T 29/49826* (2015.01)

(58) Field of Classification Search
CPC ............... A61F 2/07; A61F 2002/077; A61F 2002/072; A61F 2002/075; A61F 2220/0075; A61F 2220/0083
USPC .............................. 623/1.13, 1.14, 1.23, 1.36
See application file for complete search history.

(56) References Cited

U.S. PATENT DOCUMENTS

| | | | |
|---|---|---|---|
| 6,709,450 B2 | 3/2004 | Kang et al. | |
| 6,981,982 B2* | 1/2006 | Armstrong et al. | 606/198 |
| 2005/0159803 A1* | 7/2005 | Lad et al. | 623/1.13 |
| 2010/0161028 A1* | 6/2010 | Chuter et al. | 623/1.13 |
| 2012/0089223 A1* | 4/2012 | Nguyen et al. | 623/2.14 |

* cited by examiner

*Primary Examiner* — Todd Manahan
*Assistant Examiner* — Erich Herbermann
(74) *Attorney, Agent, or Firm* — Hoffmann & Baron, LLP

(57) ABSTRACT

A tubular prosthetic device for implantation into a body lumen includes a first part including a tubular lumen and a second part including an attachment member. The second part is secured to the first part via various configurations, where the device is capable of being reduced to a diameter less than the diameter of traditional devices, for ease of use during implantation. Methods of using the device are also provided.

8 Claims, 6 Drawing Sheets

LOW PROFILE STENT GRAFT AND DELIVERY SYSTEM

CROSS-REFERENCE TO RELATED APPLICATIONS

This application claims the benefit of U.S. Provisional Application No. 61/621,038, filed Apr. 6, 2012, the contents of which are incorporated herein by reference.

FIELD OF THE INVENTION

The present invention relates to a system for the treatment of disorders of the vasculature. Specifically, the invention relates to implantable grafts having a low profile attachment means.

BACKGROUND

The present invention relates to a system for the treatment of disorders of the vasculature, particularly aneurysms. An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aneurysms can have relatively high morbidity and mortality rates due to the risk factors inherent to surgical repair of this disease, as well as long hospital stays and painful recoveries. Due to the inherent risks and complexities of surgical repair of aortic aneurysms, endovascular repair has become a widely used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the Endurant® stent graft system manufactured by Medtronic, Inc. of Minneapolis, Minn., the Zenith® stent graft system sold by Cook, Inc. of Bloomington, Ind., the PowerLink® stent graft system manufactured by Endologix, Inc. of Irvine, Calif., and the Excluder® stent graft system manufactured by W. L. Gore & Associates, Inc. of Newark, Del. A commercially available stent graft for the treatment of TAAs is the TAG™ system manufactured by W. L. Gore & Associates, Inc.

When deploying such endovascular devices by catheter or other suitable instrument, it is advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. The profile of stent grafts may be important to achieve a favorable clinical result.

Traditional stent graft systems incorporate a full metal ring at one end of the graft, to which a stent may be attached. Although this provides securement of the stent to the graft end, it is difficult to compress the stent graft to a small size for delivery. What has been needed are stent graft systems and methods that are capable of being compressed to a small size and can be safely and reliably deployed using a flexible low profile system.

SUMMARY OF THE INVENTION

In one embodiment of the present invention, there is provided a device for implantation into a body lumen having a reduced implantation diameter, including: (a) a generally tubular first part having a lumen extending therethrough for the flow of bodily fluid, the first part including a first open end and a second open end; and (b) a second part attached to the first open end of the first part, where the second part is capable of securing the device into a body lumen; where the first open end includes an attachment flap that is compressible to a reduced diameter as compared to a device incorporating a full attachment ring, and where the attachment flap includes a plurality of attachment sites secured by a plurality of attachment tethers.

In another embodiment, there is provided a method of implanting a tubular prosthesis into a body lumen of a patient, including the steps of: (a) providing a device for implantation into a body lumen having a reduced implantation diameter, including: (i) a generally tubular first part having a lumen extending therethrough for the flow of bodily fluid, the first part including a first open end and a second open end; and (ii) a second part attached to the first open end of the first part, where the second part is capable of securing the device into a body lumen; where the first open end includes an attachment flap that is compressible to a reduced diameter as compared to a device incorporating a full attachment ring, and where the attachment flap includes a plurality of attachment sites secured by a plurality of attachment tethers.

DETAILED DESCRIPTION OF THE INVENTION

Figure 1:
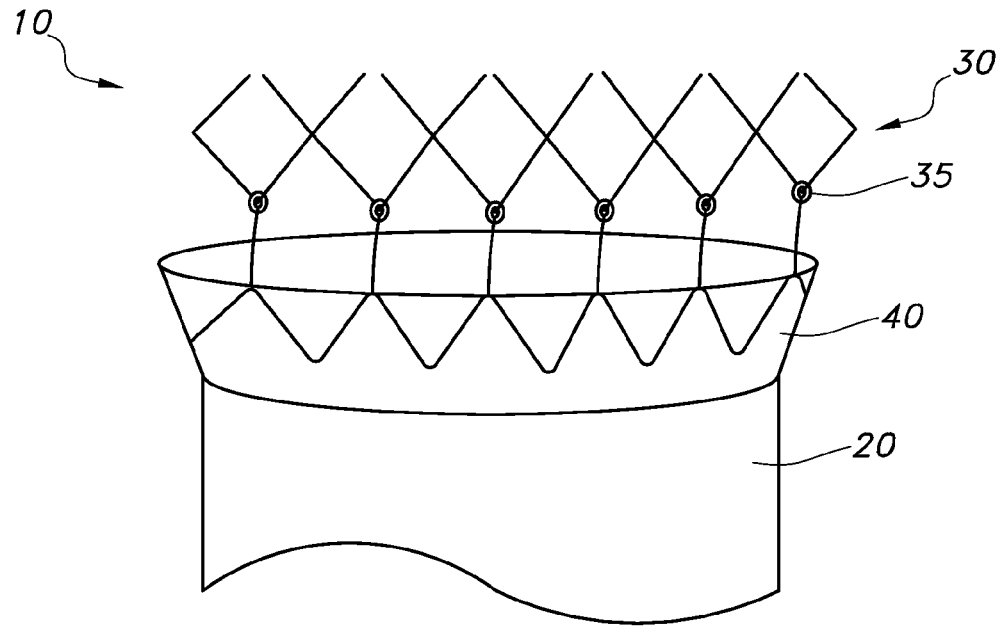
FIG. 1 is a representative embodiment of traditional stent attachment systems.

Embodiments of the invention are directed generally to methods and devices for treatment of fluid flow vessels with the body of a patient. In particular, the invention relates to devices designed for implantation into a body vessel of a patient, which allow the flow of fluid, such as blood, therethrough. Typical prosthetic devices include a first part, which is a substantially tubular member through which fluid may flow. The first part may be referred to as a graft, or a graft body. This first part is typically made of a biocompatible, substantially fluid tight material, and may include fabrics or polymers. For example, the first part may be made from materials including polytetrafluoroethylene (PTFE) or expanded polytetrafluoroethylene (ePTFE). In particular, this first part may include any number of layers of PTFE and/or ePTFE, including from about 2 to about 15 layers, having an uncompressed layered thickness of about 0.003 inch to about 0.015 inch. Unless otherwise specifically stated, the term "PTFE" as used herein includes both PTFE and ePTFE. Furthermore, the graft body sections of the present invention described herein may include all PTFE, all ePTFE, or a combination thereof. Such graft body sections may include any alternative biocompatible materials, such as DACRON, suitable for graft applications. Useful materials include, but are not limited, polyethylene; polypropylene; polyvinyl chloride; polytetrafluoroethylene; fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof.

Particularly useful materials include porous polytetrafluoroethylene either with or without a discernable node and fibril microstructure and (wet) stretched PTFE layer having low or substantially no fluid permeability that includes a closed cell microstructure having high density regions whose grain boundaries are directly interconnected to grain boundaries of adjacent high density regions and having substantially no node and fibril microstructure, and porous PTFE having no or substantially no fluid permeability. PTFE layers lacking distinct, parallel fibrils that interconnect adjacent nodes of ePTFE and have no discernable node and fibril microstructure when viewed at a scanning electron microscope (SEM) magnification of 20,000.

A porous PTFE layer having no or substantially no fluid permeability may have a Gurley Number of greater than about 12 hours, or up to a Gurley Number that is essentially infinite, or too high to measure, indicating no measurable fluid permeability. Some PTFE layers having substantially no fluid permeability may have a Gurley Number at 100 cc of air of greater than about $1 \times 10^6$ seconds. The Gurley Seconds is determined by measuring the time necessary for a given volume of air, typically, 25 cc, 100 cc or 300 cc, to flow through a standard 1 square inch of material or film under a standard pressure, such as 12.4 cm column of water. Such testing maybe carried out with a Gurley Densometer, made by Gurley Precision Instruments, Troy, N.Y.

Descriptions of various constructions of graft bodies may be found in U.S. Pat. No. 7,125,464 and entitled "Method for Manufacturing an Endovascular Graft Section", the entire contents of which are incorporated herein by reference, and in U.S. Patent Application Publication Nos. 2006/0233991, entitled "PTFE Layers and Methods of Manufacturing" and 2006/0233990, entitled "PTFE Layers and Methods of Manufacturing", the contents of all of which are incorporated herein by reference.

The second part of such devices includes an attachment member, which may be used to secure the device to the lumen into which the device is being implanted. The attachment member may be secured to one or more ends of the first part by means of a connector ring that is at least partially disposed in a wall portion of one or more ends of the first part, as will be explained in further detail below. The attachment member may be in the form of an expandable member or stent. The attachment member may be used to anchor one end of the first part (for example, the distal end or the proximal end) to the patient's vasculature. The first part may include an optional first attachment element or ring, which may be disposed adjacent one end of the first part and is configured to be securable to the attachment member to the first part. The attachment member and attachment ring, for example, may be configured as any of the attachment elements in U.S. Patent Application Publication No. US 2005/0228484 A1, which is hereby incorporated by reference herein in its entirety.

In one embodiment, the second part may include a tubular stent, which joins the first part to the lumen into which it is implanted. The stent may be self-expanding or may be expandable upon force, such as through a balloon. The stent may also optionally include barbs that are angled outwardly from the attachment member and are configured to engage tissue of the vessel wall of the patient, and prevent axial movement of the device once deployed. In use, the device is typically implanted into the lumen and held in place, at which time the stent is expanded to secure the device to the inside of the body lumen, allowing flow of fluid therethrough. Stent attachment means are particularly useful because stents allow for quick, accurate and safe implantation, while avoiding the need to suture or otherwise surgically secure the device in place. A stent attachment member is typically secured to the first part by means of an attachment ring, which spans the circumference of the first part and secures the stent to the first part. However, the present invention provides devices in which the second part, including attachment member, may be secured to the first part without the need for a typical attachment ring.

Devices such as that disclosed herein are typically implanted into the patient's body through the use of a catheter or other implantation device, which travels through the body lumen and allows deployment of the device therein. As will be understood to those of ordinary skill in the art, since the deployment of the device is conducted through the body vessel, the device must typically be compressed or rolled such that it has a small diameter. Prior art devices have typically only been able to achieve a compressed thickness of 18-25 French. The present invention, however, has been able to achieve much smaller diameters in a compressed or rolled condition. The compressed or rolled diameter of the present invention is about 9 French to about 15 French, and more specifically from about 11 French to about 14 French. The small diameter allows the device to travel through the body lumen safely and accurately. Devices are typically rolled or compressed into a small diameter, placed into the catheter, and led through the vessel into position, where the catheter releases the device. Thus, a small diameter is important to success in implantation. However, when the device to be implanted includes a securement device attached thereto, such as a stent member, it is often difficult to achieve the small diameter desired for implantation. This is particularly true when the first part of the device includes a full attachment ring, as depicted in FIG. 1.

FIG. 1 depicts a traditional device, including a first part secured to a second part via a full attachment ring. As seen in FIG. 1, a traditional implantable device 10 includes a first part 20, which is a generally tubular member made of a fluid tight material or materials as discussed above, and a second part 30, which is used to secure the device 10 to the inside of a body lumen. In embodiments including such a separate second part 30, the second part 30 is typically a tubular stent member, which may be made from any number of materials, including polymeric materials, metals, and combinations thereof. The second part 30 may be joined to the first part via securement anchors 35, which may include eyelets, hooks, holes, snaps, "dog-bone" configurations, and combinations thereof.

As will be understood, of course, the use of a separate first part 20 and second part 30 in these devices 10 requires a means to secure the first part 20 and the second part 30 to each other in such a manner that the two will not become separated either during the implantation process or after implantation is complete. To achieve this securement, the device 10 will oftentimes include an attachment ring 40, which is disposed at one or more open ends of the first part 20, and which travels the entire circumference of the first part 20. The attachment ring 40 is typically a continuous ring of solid material, sometimes having a wave pattern, which spans the entire circumference of the first part 20. The attachment ring 40 is usually made of similar materials as the second part 30, including solid metals and polymeric materials, which aid in providing a secure attachment of the first part 20 and second part 30. The attachment ring 40 is typically embedded in a polymeric region, located at one or more ends of the first part 20. The second part 30 is secured to the attachment ring 40 via a plurality of securement anchors 35, which may include eyelets, hooks, holes, snaps, "dog-bone" configurations, and combinations thereof.

As can be appreciated, the presence of a full attachment ring 40 at one or more ends of the first part 20, spanning the entire circumference of the first part 20, renders the collapsing and compression of the device 10 difficult to achieve. This is especially true when the attachment ring 40 is made of solid metal or polymeric materials, and has a significant wave shape. Although such devices are somewhat capable of being compressed to suitable sizes, it is often difficult and cumbersome to deploy such devices in a safe and economic manner. The present invention is directed to devices which include a suitable means for attachment of a tubular graft to a stent member, but which avoid the problems associated with such traditional devices as seen in FIG. 1.

For ease of understanding, FIGS. 2 through 9 herein depict various embodiments of attachment of the first part to the second part. It will be understood that the first part and/or the second part may extend to any desired length or shape. In the description below, the term "first part" is intended to include a generally tubular lumen through which a fluid may flow, such as a graft and/or stent graft. The first part may be made of any desired material, such as PTFE, ePTFE, Dacron, and combinations thereof. The first part may be a tubular graft including two opposed open ends, or it may include more than two open ends (for example, a bifurcated or trifurcated graft having more than two open ends). In the description below, the term "second part" is intended to refer to a means or mechanism that is secured to the first part, and that aids in securing the device in the patient. In some embodiments, the term "second part" includes an expandable stent member, which may be self-expanding or may be expandable upon inflation of a balloon. The desired stent member may be made from any desired materials, including metallic and polymeric materials, and may include additional attachment features, such as barbs, hooks, and the like. The second part may have a general mesh design typically used in stents. In general, tubular grafts and stents are known and understood to those of skill in the art, and the present invention provides safer, more secure ways to attach the two together to form a reduced diameter device upon implantation. Reduction in the diameter of devices upon implantation is beneficial to allow for a safer, more accurate and secure implantation of the device.

Figure 2:
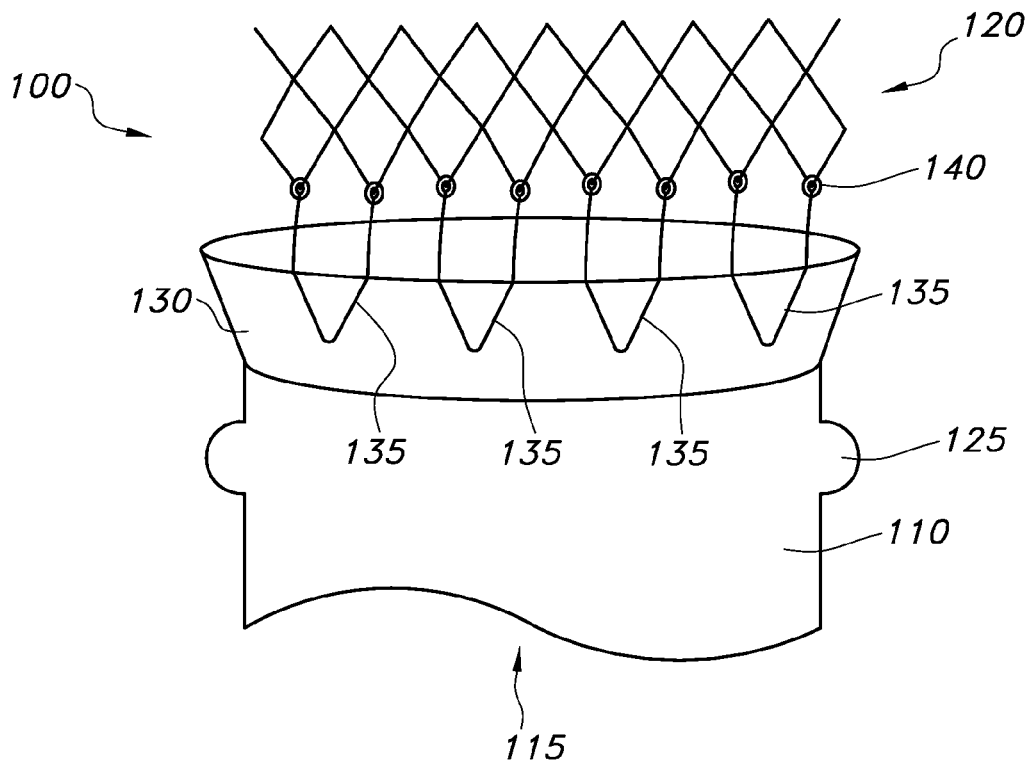
FIG. 2 is a representation of one embodiment of the invention incorporating a reduced size attachment flap design.

FIG. 2 depicts one embodiment of the present invention, providing a device 100, which is capable of having a low profile when compressed. As with typical devices described above, the inventive device 100 includes a first part 110, which is a generally tubular, fluid flowable component having an inner lumen 115. The first part 110 may be any size or length desired, and typically will be selected to be substantially similar to the body vessel into which the device 100 is being implanted. The first part 110 may be made from any desired biocompatible materials known to those of ordinary skill in the art, including, for example, PTFE, ePTFE, Dacron, ultra high molecular weight polyethylene, and combinations thereof. The first part 110 may be a stent-graft, if desired. The first part 110 may be tubular and have two opposed open ends defining a straight lumen, or it may be split, having more than two open ends (i.e., bifurcated, trifurcated, etc.). The number of open ends in the first part 110 is not critical, and any number may be selected. For purposes of the present invention, discussion will be made of only one open end of the first part 110, although it should be understood that the inventive attachment means may be disposed at any or all of the open ends of the first part 110.

This embodiment includes a second part 120 at the end of the first part 110. Preferred configurations for the second part include a stent member, having a generally tubular, open mesh design. The second part 120 may be approximately the same diameter as the first part 110 when opened, or it may have a larger or smaller diameter. The second part 120 may include any desired materials, including, for example metals (such as nitinol), polymers, and combinations thereof. The second part 120 may be self-expanding. In such embodiments, the second part 120 has a natural tendency to expand to its fully open state, which aids in securement of the device 100 to the body lumen. Alternatively, the second part 120 may be expandable upon the exertion of force, such as through the use of an inflatable balloon or other opening means. The second part 120 may have barbs or other components that aid in securement of the device 100 to the body lumen, if desired. Further, the second part 120 may be any length desired, so as to effectively secure the device 100 in place after implantation.

In some embodiments, the first part 110 includes at least one inflatable channel 125, which may be inflatable with a biocompatible material and used to aid in attachment of the device 100 to the body. The inflatable channel 125 may, for example, be inflated such that it is pressed against the inside surface of the body lumen into which it is being implanted, thereby providing additional securement and/or sealing of the device 100 in place. The Figures set forth herein will each include one inflatable channel 125, although it is understood that this feature is optional and may be omitted, or alternatively that there may be more than one inflatable channel 125.

In this first embodiment set forth in FIG. 2, the second part 120 may be joined to the first part 110 by means of a reduced size attachment flap 130. As with prior art devices, the reduced size attachment flap 130 is used to secure the second part 120 to the first part 110. The reduced size attachment flap 130 is generally made of a polymeric material, and may be made from the same material as the first part 110 if desired. Although FIG. 2 depicts the reduced size attachment flap 130 as a separate piece from the first part 110, it will be understood that the reduced size attachment flap 130 may simply be the end of the first part 110, without the need for a separate structure. For example, the reduced size attachment flap 130 may be the end of the first part 110 folded over itself to form a cuff. As another alternative, the flap 130 may be helically wound about the shape forming mandrel to form its structure Some exemplary methods of forming a tubular PTFE structure is described in U.S. Pat. No. 7,125,464 and entitled "Methods and Apparatus for Manufacturing an Endovascular Graft Section"; U.S. Pat. No. 7,090,693 and entitled "Endovascular Graft Joint and Method of Manufacture"; and U.S. Pat. No. 6,776,604 and entitled "Method and Apparatus for Shape Forming Endovascular Graft Material", all to Chobotov et al., the complete disclosures of which are incorporated herein by reference. Other means to secure the first part to the second part include the use of a tethered arrangement, which will be described in further detail below.

In contrast to prior devices, however, the reduced size attachment flap 130 includes a series of discrete, separate ring members 135, which cooperatively span the circumference of the first part 110, but are not connected to each other. Each of these ring members 135 may be made from a solid material, and may be made from similar materials as the full attachment ring typically used in such devices. Each of the ring members 135 are desirably embedded in a polymeric material at the open end of the first part 110, thus ensuring securement of the ring members 135 to the first part 110. The ring members 135 may have a general "V" shape, with the ends of the "V" disposed at the open end of the attachment flap 130, although any shape may be used, such as a "U" or "W" shape.

The ring members 135 may include an elongated portion, which extends beyond the edge of the attachment flap 130, having an optional securement member 140 at the end. It may be desired that the second part 120 is directly secured to the first part 110 without the use of an optional securement member 140. If used, the optional securement member 140 may be used to secure the second part 120 to the ring members 135 in any desired means. In one embodiment, the optional securement member 140 may be a general "dog-bone" type of securement, which is used to couple the second part 120 to the ring members 135. The optional securement member 140 may include any attachment design desired, including, for example, eyelets, hooks, holes, snaps, "dog-bone" configurations, and combinations thereof.

The reduced size attachment flap 130 is beneficial in that it provides an adequate and secure method of attaching a second part 120 (i.e., a stent member) to the first part 110, while minimizing the amount of ring material in the device 100. The reduced size attachment flap 130, with its discrete, separate ring members 135, includes a lesser amount of solid material and includes a greater amount of polymeric graft material, and thus can be compressed to a greater degree than designs that include a full ring spanning the entire circumference of the first part 110. As mentioned above, the present invention is capable of compressing the device to a compressed or rolled diameter of from about 9 to about 15 French (about 3-5 mm), and more particularly from about 11 to about 14 French.

In use, the second part 120 is secured to the first part 110 via the reduced size attachment flap 130. The device 100 may then be compressed (such as via rolling) to a smaller diameter. The compressed device 100 may be fed into a catheter, and led through the body vessel to the implantation site. The device 100 may then be released from the catheter at the site of implantation, and the second part 120 expanded to secure the device 100 in place. The first part 110 and second part 120 are held together in a secure fashion by the reduced size attachment flap 130, ring members 135 and securement members 140.

Figure 3:
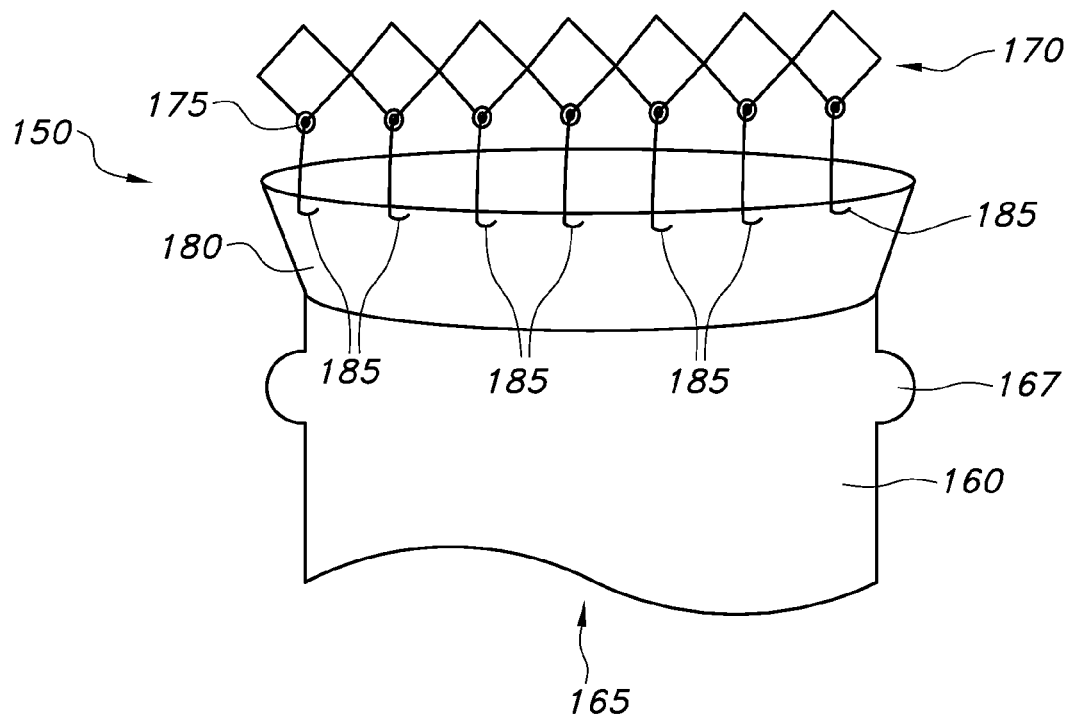
FIG. 3 is a representation of an alternative embodiment of the invention incorporating a single point attachment of the stent to the graft.

In another embodiment, generally set forth in FIG. 3, a device 150 including a first part 160 having a generally tubular shape with a lumen 165 therethrough, as described above, and a second part 170, as described above, is provided. As with above, the first part 160 may be made from a biocompatible material, such as ePTFE, PTFE, Dacron, ultra high molecular weight polyethylene, and combinations thereof. As with above, the second part 170 may be a tubular stent member, but may include any desired attachment device desired. Further, the second part 170 of this embodiment may be disposed at one or all open ends of the first part 160, as described above. In addition, the first part 160 may include zero, one, or more than one inflatable channels disposed at one or more ends, which may aid in providing attachment and sealing of the device 150 to the lumen into which it is implanted.

In this embodiment, as described above, the second part 170 is secured to the first part 160 at an attachment region 180. The attachment region 180 may be a separate piece of material, or it may be integrally formed with the first part 160. In some embodiments, the attachment region 180 may simply be the end of the first part 160 or the attachment region 180 may be the end of the first part 160 folded over itself to form a cuff. The attachment region 180 may be made from a polymeric material having a discrete node and fibril structure, such as expanded PTFE. In this embodiment, the second part 170 is secured to the first part 160 through use of a series of individual attachment members 185 having a hook-like feature at one end thereof. The second part 170 may be directly secured to the first part 160, or may include an optional connector 175. Optional connector 175 may include any of the configurations described above (i.e., eyelet, hook, "dog-bone", and the like).

Each of the attachment members 185 includes a securement feature at its end, such as a hook, barb, or other latching feature, which may be embedded into the attachment region 180. In embodiments where the attachment region 180 is made from a material having a node and fibril structure, such as expanded PTFE, the attachment region 180 will include a series of nodes and fibrils. The securement feature of the attachment member 185 extends into the attachment region 180, where it may be hooked onto one or more fibrils. Through attachment of the securement feature to the fibrils, a secure connection may be made between the first part 160 and the second part 170.

As with the first embodiment, in use, the second part 170 is secured to the first part 160 via the attachment region 180. The device 150 is then compressed (such as via rolling) to a smaller diameter. The compressed device 150 may be fed into a catheter, and led through the body vessel to the implantation site. The device 150 may then be released from the catheter at the site of implantation, and the second part 170 expanded to secure the device 150 in place.

Figure 4:
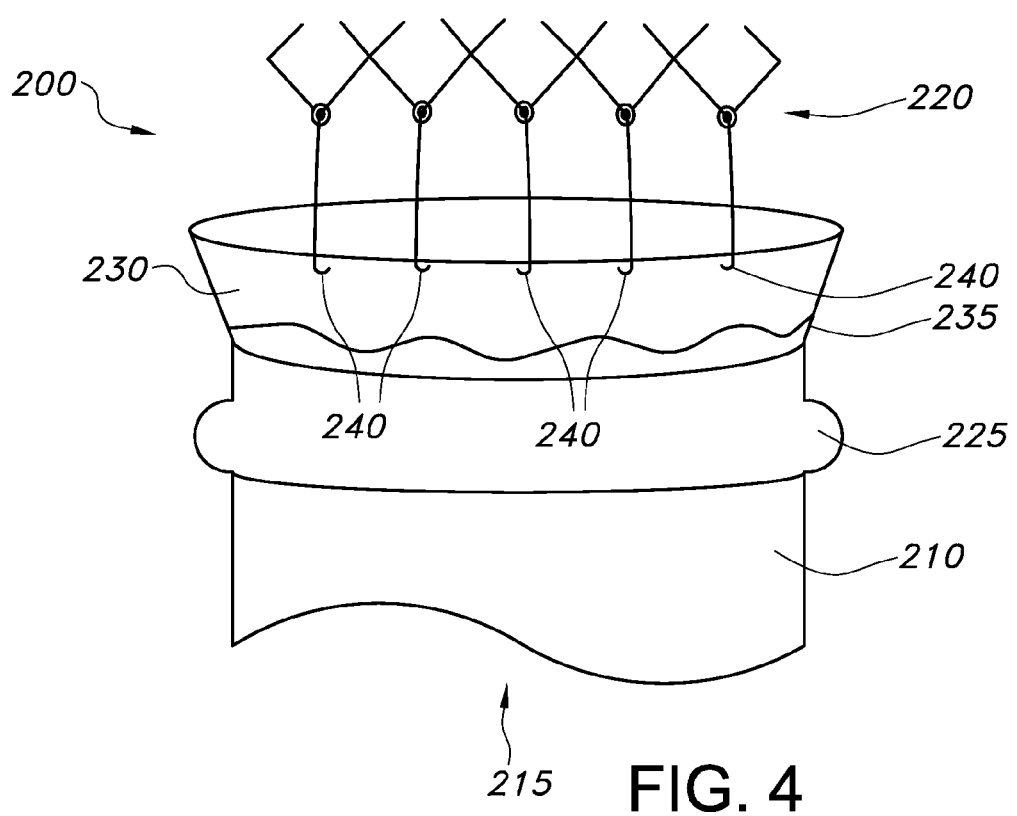
FIG. 4 is a representation of an alternative embodiment of the invention including a radially expandable ring and a single point attachment of the stent to the graft.

FIG. 4 depicts yet another embodiment of the present invention, which includes an implantable device 200, including a first part 210 as described above and a second part 220 (i.e., a stent) as described above. The first part 210 is a graft made from biocompatible materials, and generally includes a flowable lumen 215 extending therethrough. Optionally, the first part 210 may include one or more inflatable channels 225, which may aid in providing attachment and sealing to the body vessel into which the device 200 is implanted.

In this embodiment, the second part 220 is secured to the first part 210 via a hybrid attachment region 230. The hybrid attachment region 230 is made from a polymeric material, such as PTFE or expanded PTFE, and may be integrally formed with the first part 210. In some embodiments, the hybrid attachment region 230 may be formed through folding the end of the first part 210 over itself to form a cuff. The hybrid attachment region 230 includes a reduced size ring 235, which spans the circumference of the hybrid attachment region 230, but does not extend to the outer edge of the hybrid attachment region 230. The reduced size ring 235 is made from a material that has a tendency to expand radially outward, and thus provides a means for maintaining the open end of the first part 210 in an open state. The reduced size ring 235 may be made from any desired material, including, for example, metals such as nitinol or polymeric materials. The reduced size ring 235 may include a general "W" shape and being sinusoidal in form. Notably, the reduced size ring 235 is sufficiently small that it will not impede compression of the device 200, but will be strong enough to aid in expansion of the device 200 when implanted.

In addition to the reduced size ring 235, the device 200 may also include a second part 220 including includes a series of individual attachment members 240 at one end thereof. The second part 220 is secured to the first part 210 via the attachment members 240, as described previously in FIG. 3. Each of the attachment members 240 may include a securement feature at its end, such as a hook, which is embedded into the hybrid attachment region 230. In embodiments where the hybrid attachment region 230 is made from a material having a node and fibril structure, such as expanded PTFE, the hybrid attachment region 230 will include a series of nodes and fibrils. The securement feature of the attachment member 240 extends into the hybrid attachment region 230, where it may be hooked onto one or more fibrils. Through attachment of the securement feature at the end of the attachment member 240 to the fibrils, a secure connection may be made between the first part 210 and the second part 220.

In some embodiments, the reduced size ring 235 may not be used to directly attach the second part 220 to the first part 210. Attachment of the second part 220 to the first part 210 may optionally be achieved through the use of securement features on the attachment members 240, which are secured in the hybrid attachment region 230. The reduced size ring 235 is present to aid in expansion of the device 200 and maintaining the end of the first part 210 in an open state so as to allow fluid flow therethrough. In this embodiment, the reduced size ring 235 contains less metal or other hard material than in traditional device (such as that described in FIG. 1), and thus may be compressed to a smaller diameter than in traditional devices.

In some embodiments, instead of a securement via attachment members 240, the second part 220 may be secured to the first part 210 through the use of a hybrid attachment ring 230, with supported attachment configurations, as will be described below.

Figure 5A:
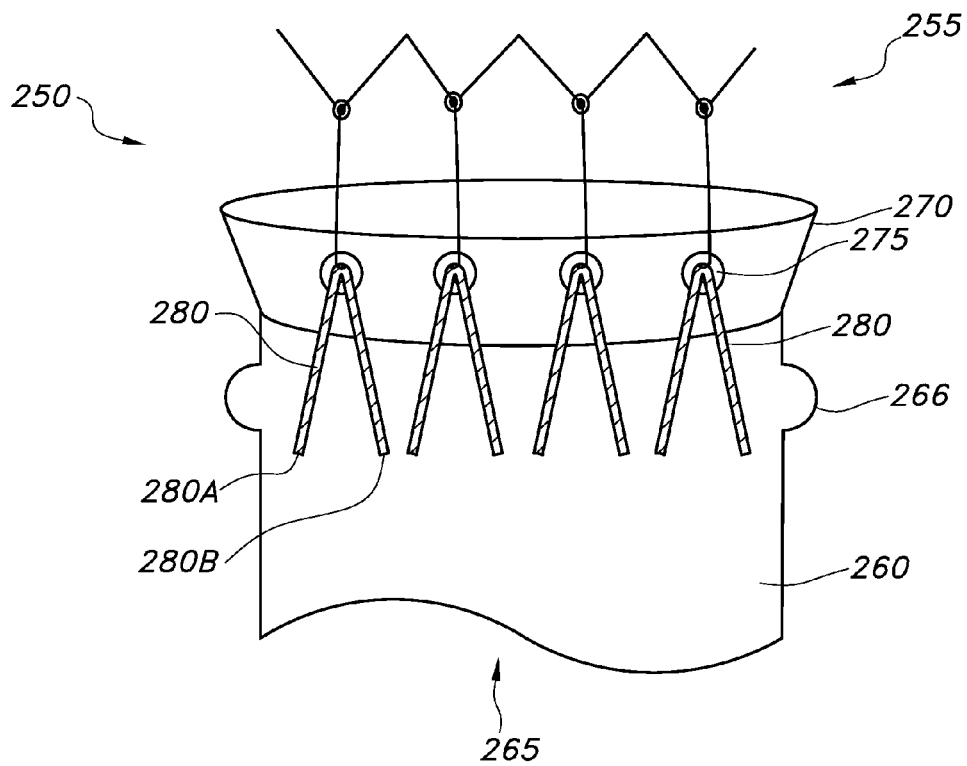
FIGS. 5A and 5B are each a representation of yet another embodiment of the invention including single point attachments of the stent to the graft using a supported hole and optional tethered design.
Figure 5B:
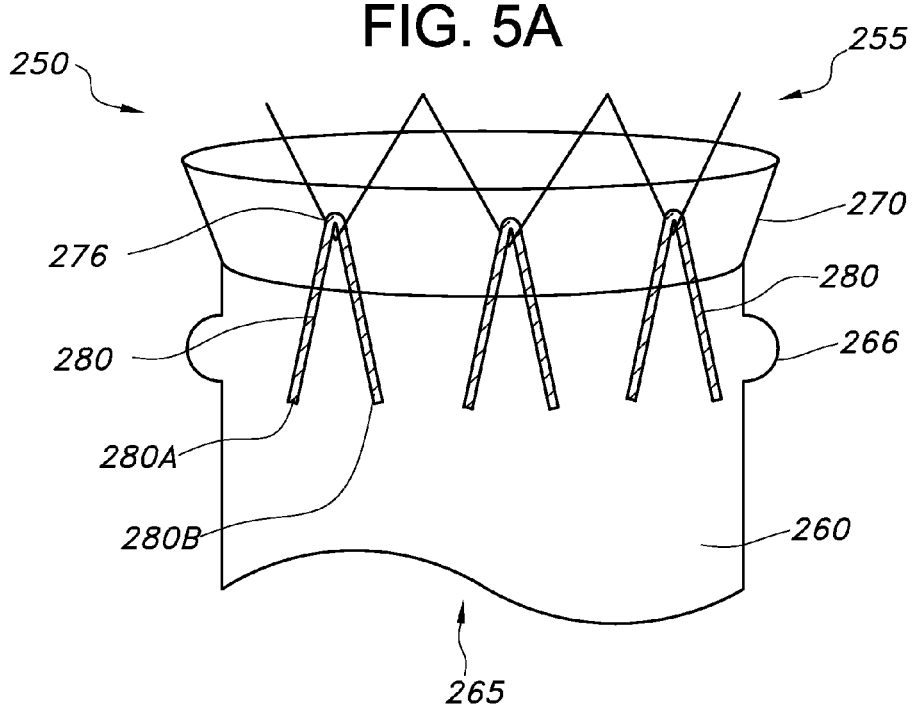

FIGS. 5A and 5B depicts different embodiments of a device 250 using a supported attachment configuration for securement of a second part 255 to a first part 260 including a tethered arrangement. The first part 260 is described above, having a lumen 265 generally extending therethrough and may include an optional inflatable channel 266, as explained above. The second part 255 includes a general stent configuration described above. The configuration includes an attachment flap 270, also as described above. The embodiment of FIG. 5A additionally depicts a reinforced filament configuration, which may be useful in providing a secure, low profile design. In this embodiment, the attachment flap 270 includes a series of reinforced attachment sites 275 secured by attachment tethers 280. There may be any number of attachment tethers 280 and attachment sites 275 around the periphery of the attachment flap 270. As can be seen, the second part 255 is directly secured to the first part 260. However, in some embodiments, the attachment sites 275 may secure a plurality of optional securement members, which in turn, secures the second part 255. FIG. 5B depicts an embodiment in which there is no reinforced attachment site, but rather the tethers 280 directly secure the second part 255 at securement site 276, such as by intertwining and/or interlacing the tether 280 and the second part 255, or using a looped configuration. Furthermore, the tethers 280 themselves may be intertwined and/or interlaced with one and the other or even just placed over one and the other. For example, one portion of the tether 280 may be laid over and/or under another portion the tether 280. Such interlacing in an under-and-over arrangement may take a form of a braid of portions of the tethers 280. The second part 255 may be directly attached to the first part 260, however, in some embodiments, the second part 255 may be secured by using a general "dog-bone" or other securement configuration.

The attachment tethers 280 may be made of PTFE and/or ePTFE, or any other material desired. The attachment tethers 280 may be formed integrally with the first part 260, or they may be a separate feature that is attached to the first part 260. As can be seen in FIGS. 5A-5B, each tether 280 is made of a first strand 280A and second strand 280B, which are each secured to either the reinforced attachment site 275 or securement site 276. The first strand 280A and second strand 280B may be a single unitary strand, forming the tether 280 such as by looping through the attachment site 275. Alternatively, the first strand 280A and second strand 280B may be separate pieces, which are separately secured to the attachment site 275 or securement site 276. The tether 280 can include a single unitary piece whereby first strand 280A and second strand 280B are made from one single piece. If desired, the attachment sites 275 may be secured to the attachment tethers 280 through the use of fluorinated ethylene propylene (FEP) dispersion, which may provide improved bonding. The device 250 may include alternate securement features such as eyelets at the attachment sites 275 or securement sites 276, such as that seen in FIG. 5A. In this embodiment, a tether 280 may directly secure the second part 255 through eyelets at the attachment site 275. The eyelet may optionally be formed as an integral part of the second part 255, if desired. That is, the end of the second part 255 in contact with the first part 260 or attachment flap 270 may include a plurality of eyelets for securement of the tethers 280. For example, when the second part 255 is a stent, the end of the stent may include a plurality of eyelets configured to allow tethers to secure therein.

Alternative and/or additional securement methods include adhesives, heat, compression, welding, sintering, and combinations thereof. Welding may include circumferential, substantially circumferential and/or partial circumferential weld lines (not shown) in the portions of the attachment flap 270 and/or in portions of the first part 260 across or partially across portions of the tethers 280. Through the use of a tethered arrangement, the tethers may provide an improved strength of attachment of the second part. In particular, each attachment point may provide a strength of about 4 to about 10 pounds-force (lbf). Using a plurality of tethered arrangements will improve the strength by multiplying the number of tethers by the individual strength (about 4-10 lbf.).

It is to be understood that the device 250 may include a reduced size attachment flap 270 with supported ring members as described above in other embodiments, in addition to the tethered configuration. For example, it may be desired to include a design that includes a series of separate and discrete ring members for support, but use attachment sites 275 and attachment tethers 280 for securing the second part (and vice versa).

Figure 6A:
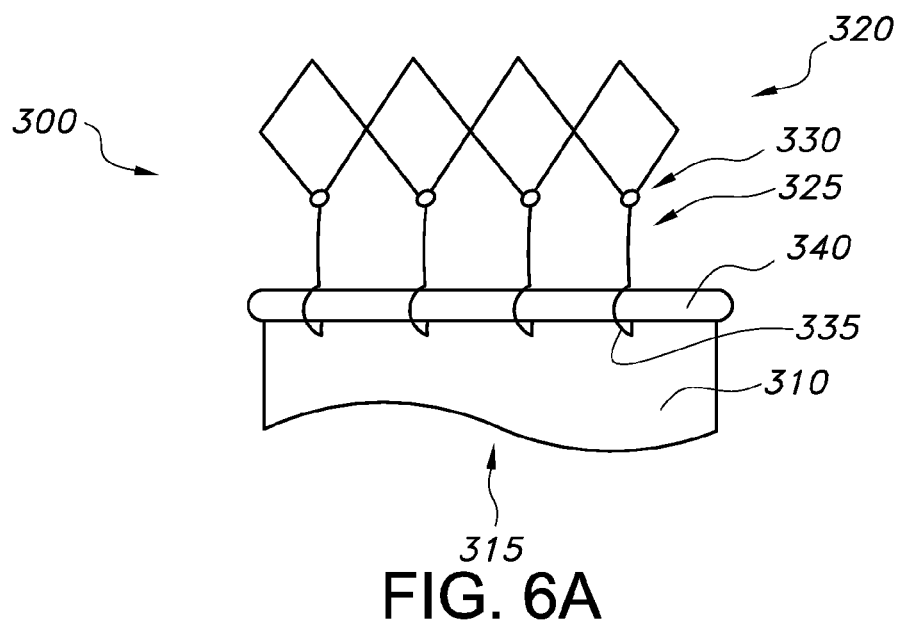
FIG. 6A is a side view of yet another embodiment of the invention including a single point attachment of the stent to the graft with a supporting roll feature.
Figure 6B:
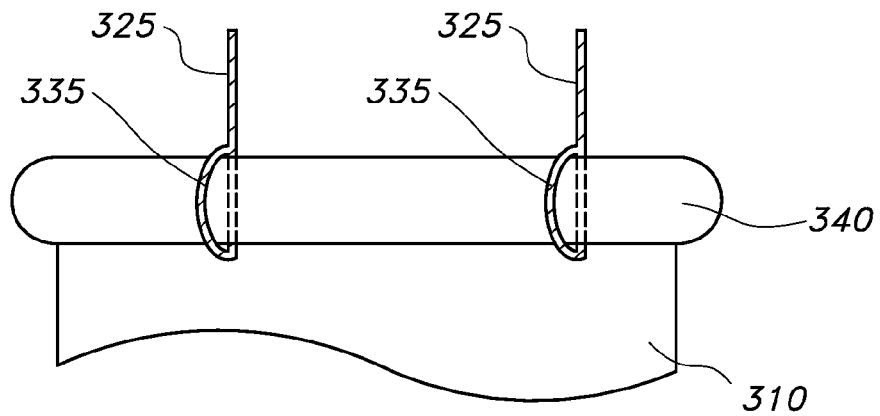
FIG. 6B is a close up of the supporting roll feature of FIG. 6A.

FIG. 6BA depicts yet another embodiment of the low profile device, including a supporting roll feature, which provides added strength and security to the attachment. As with the previous embodiments, the device 300 includes a first part 310, which is a generally tubular prosthetic material having a lumen 315 extending therethrough, and a second part 320, which is designed to secure the device 300 in place upon implantation. As with above, the second part 320 can be a stent, and may be either self-expanding or expandable upon force, such as through use of an inflatable balloon. The securement of the second part 320 to the first part 310 in this embodiment is achieved through the use of a series of attachment members 325, which may be part of a unitary structure forming the second part 320. In some embodiments, the second part 320 is directly secured to the first part 310, however, in other embodiments, the second part may have a plurality of optional securement features 330 at a first end and a supported hook 335 at the second end. The attachment members 325 may be made from any material desired, such as metals, polymers, and combinations thereof. The optional securement feature 330, when present, may include any securement features described above, such as eyelets, hooks, "dog-bone" configurations, and the like.

The supported hook 335 secures the attachment member 325 to the first part 310, and may best be seen in FIG. 6B. The second end of the attachment member 325 includes a general hook-like configuration forming a supported hook 335. The first part 310 includes a generally tubular configuration about the circumference at one end, forming a supporting roll or lip 340. The supporting roll 340 may be made from the same material as the first part 310, including, for example, PTFE and/or ePTFE, but has a slightly larger circumference than the rest of the first part 310. In some embodiments, the supporting roll 340 is a separate part, which may be attached to the first part 310, or alternatively, the supporting roll 340 may be formed from the first part 310, i.e., by rolling one end of the first part 310 over itself. Although the supporting roll 340 may be made from a polymeric material, in some embodiments, the supporting roll 340 also may be made from metallic materials.

In use, the supported hook 335 is placed about the supporting roll 340, such that the supported hook 335 is secured in place by the supporting roll 340. In some embodiments, the supported hook 335 extends completely around the supporting roll 340, providing a secure and strong attachment thereto. It is particularly desirable that the supporting roll 340 be sufficiently strong so as to withstand pull of the supported hook 335 without tearing or otherwise breaking.

Figure 7:
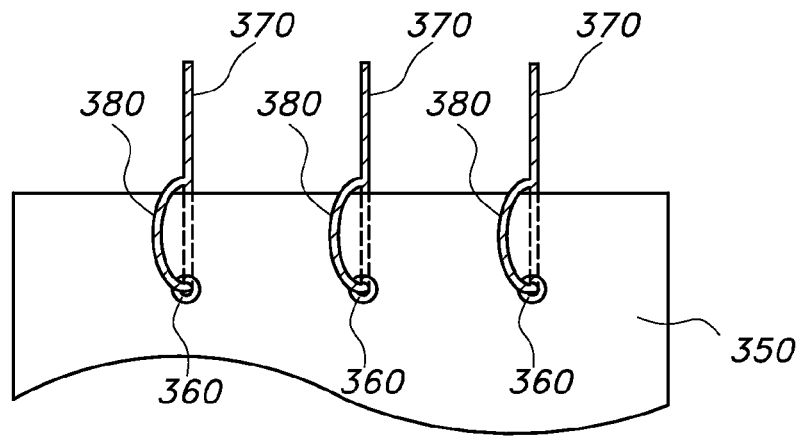
FIG. 7 is a close up of yet another embodiment of the invention including a single point attachment of the stent to the graft with a reinforced hole feature.

FIG. 7 depicts a similar attachment embodiment to FIG. 6, but instead of a supporting roll, the first part 350 includes a series of reinforced holes 360 at one end. In this embodiment, the end of the first part 350 to be secured to a second part (not shown) includes a series of reinforced holes 360. The reinforced holes 360 may be formed via any desired method, and made be made from any desired materials, such as polymeric or metallic materials. The reinforced holes 360 typically are sufficiently strong to withstand pulling without tearing or breaking. In use, a plurality of attachment members 370, each having a secured hook 380, are placed through the plurality of reinforced holes 360, such that each attachment member 370 is secured into one reinforced hole 360. As with the embodiments described above, a second part (i.e., a stent) is secured to the attachment members 370 via any attachment configuration desired.

In some embodiments, instead of reinforced holes 360, the reinforcement may be achieved through a series of reinforced tabs or similar features. The ultimate goal of this embodiment is to provide a series of discrete points of attachment, which are strong enough to withstand tearing or ripping of the first part 310 upon pulling of the attachment members 370. In these embodiments, the use of a full attachment ring (such as that described in FIG. 1 above) may be avoided, allowing the devices to be compressed to a smaller diameter for insertion into a patient's body.

Figure 8A:
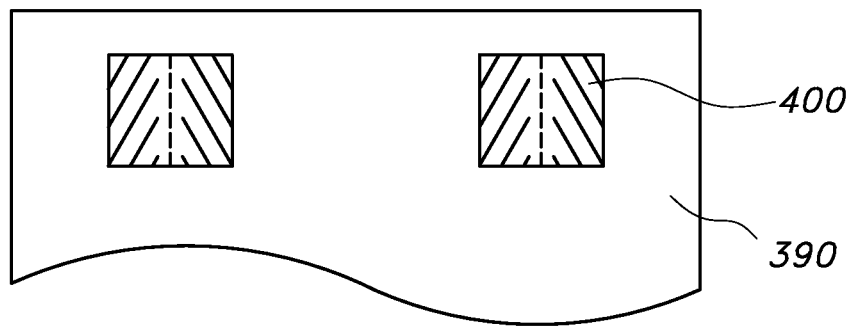
FIGS. 8A and 8B depict an embodiment of the present invention including a series of reinforcement tabs to secure a stent to a graft.
Figure 8B:
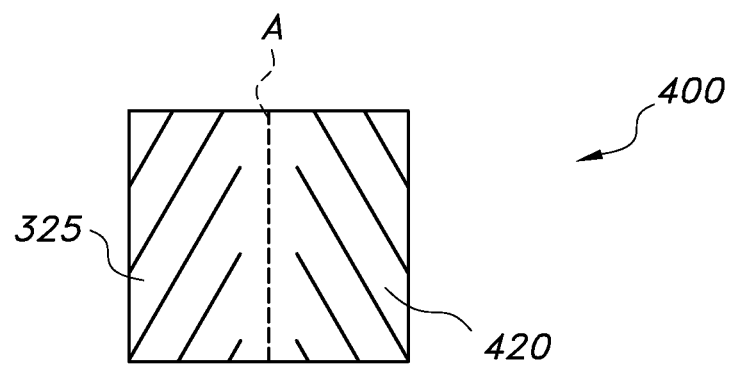

FIGS. 8A and 8B depict an attachment using a series of reinforcement tabs 400. In such an embodiment, the first part 390 includes, at a plurality of securement points, a series of reinforcement tabs 400. The reinforcement tabs 400 may be disposed about the periphery of the first part 390, and there are, e.g., at least 5 reinforcement tabs 400 about the first part 390. A reinforcement tab 400 may be present at each location of attachment of the second part (not pictured) to the first part 390.

The reinforcement tabs 400 are designed to provide a high degree of tear resistance in the axial direction. As is understood by those of skill in the art, securement of the second part to the first part 390 may be via hooks or any other securement means. However, if the second part is pulled in a direction away from the first part 390, there is a risk that the first part 390 may tear or rip. Reinforcement tabs 400 aid in providing strength to the device, thus reducing the risk of tearing or ripping the first part 390.

Reinforcement tabs 400 may be made from a polymeric material such as, expanded PTFE. As can best be seen in FIG. 8B, the reinforcement tab 400 includes two different orientations of nodes and fibrils, so as to provide a more secure attachment. In particular, the reinforcement tab 400 includes a first section 410 and second section 420, which are separated in approximately the middle of the reinforcement tab 400 along an axis A. In use, the axis A will substantially be in alignment with the axis of the first part 390. The first section 410 includes a series of nodes and fibrils that are oriented in a direction that is about 1° to about 60° offset from the axis A. The second section 420 includes a series of nodes and fibrils that are oriented in a direction that is about 1° to about 60° offset from the axis A, in the opposite direction as the nodes and fibrils of the first section 410. In another embodiment the nodes and fibrils of the first section 410 are oriented about 20° to about 50° offset from the axis A, such as about 30° offset from the axis A. Similarly, the nodes and fibrils of the second section 420 are oriented about 20° to about 50° offset from the axis A, such as about 30° offset from the axis A (in the opposite direction from the nodes and fibrils of the first section 410). The angle of the nodes and fibrils in the first section 410 is approximately the same as the angle of the nodes and fibrils in the second section 420, in the opposite direction, with the axis A separating each section 410, 420.

The resulting reinforcement tab 400, as seen in FIG. 8B, has a series of nodes and fibrils in the first section 410 and the second section 420 that are offset from the axis A in opposite directions at about the same angle. The angles of each node and fibril orientation can be about 30° offset from the axis A, thus creating an angle between the nodes and fibrils of the first section 410 and the nodes and fibrils of the second section 420 of about 60° therebetween. The second part (not pictured) may be secured to the first part 390 at the reinforcement tabs 400, and may be at a location near the axis A of the reinforcement tab 400. In this manner, the second part may pull in a direction away from the first part 390, without risk of tearing the first part 390.

The reinforcement tab 400 may be made as a separate piece, which may then be secured to the first part 390 via any desired means, including, for example, lamination, adhesives, threading, and combinations thereof. The reinforcement tab 400 may be made as a single unitary piece, or it may be made as separate pieces attached together. If the reinforcement tab 400 is made as a single unitary piece, it may be formed through a two-stage stretching process, where the first section 410 is stretched in a first direction and then the second section 420 is stretched in a second direct, as described above. Alternatively, the reinforcement tab 400 may be formed from two separate pieces, which are then attached together, with the first piece forming the first section 410 and the second piece forming the second section 420. In this fashion, the two pieces can be stretched in their respective directions and then secured together to form the two-section reinforcement tab 400 through any desired means, including, for example, lamination, adhesives, threading and combinations thereof.

Figure 9:
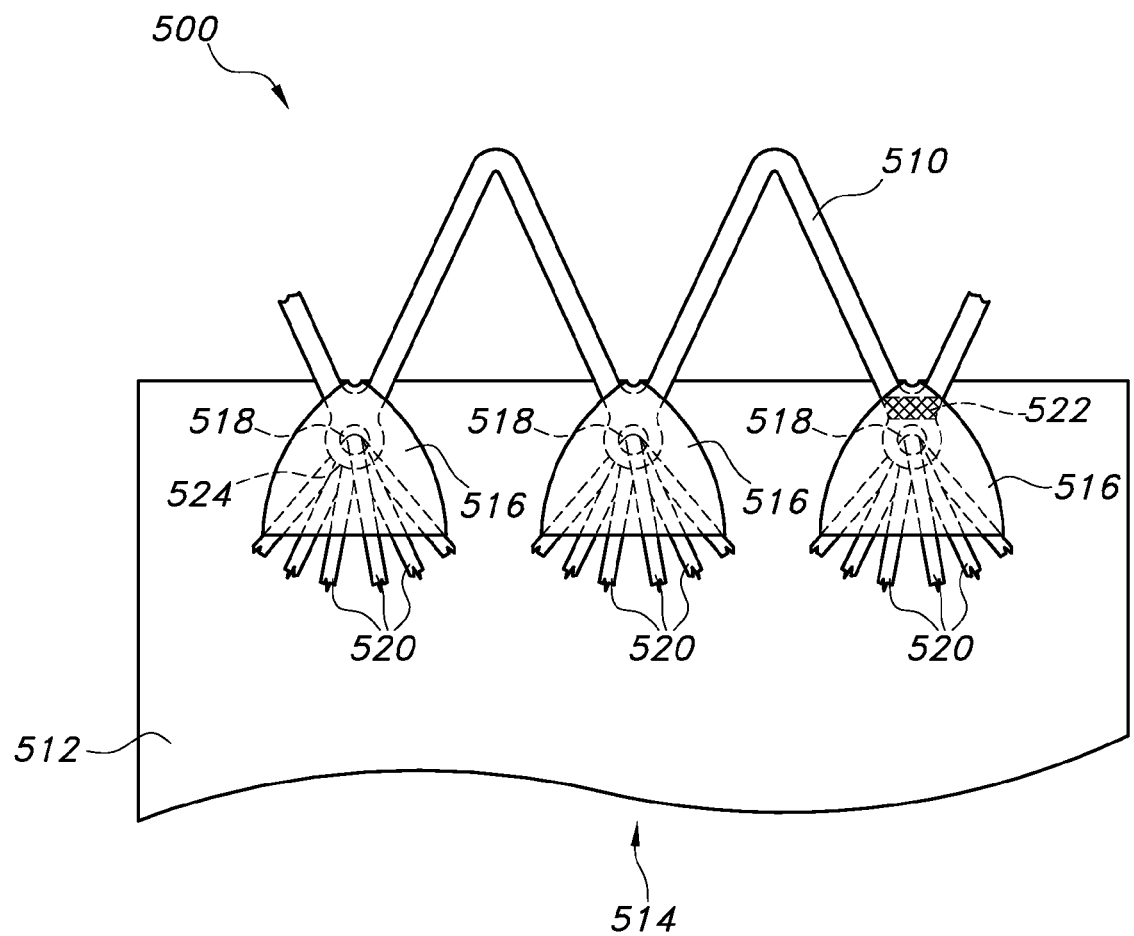
FIG. 9 depicts an embodiment of the present invention including folded-over graft material to secure a stent to a graft.

FIG. 9 depicts another embodiment of the present invention. A device 500 using a supported attachment configuration for securement of a second part 510 to a first part 512 including a tethered arrangement. The first part 510 is for example a graft as described above, having a lumen 514 generally extending therethrough and may include an optional inflatable channel (not shown), as explained above. The second part 510 includes a general stent configuration described above. The configuration includes an eyelet 518 formed in lower apices 524 of the second part 510 with tethers 520 disposed through the eyelets 518. Although, as depicted in FIG. 9 each of the apices 524 has any eyelet 518, the present invention is not so limited. The tethers 520 may be formed from any of the above-described materials may be formed by any of the above-described materials and may be secured by any of the above-described techniques. The configuration further includes a portion of graft material 516 overlaying the apices 524, the eyelets 518 and at least portions of the tethers 520. The graft material 516 may be graft material from the interior surface of the graft lumen 514 or graft material from an internal portion, typically from a layer or layers of graft material which are laminated to for the second part 510, folded over the apices 524, the and eyelets 518 and the tethers 520. Although multiple tethers 520 are depicted in FIG. 9, the present invention is not so limited, and any suitable number of tethers, including just one tether, may be used. The portion of graft material 516 may be secured to the first part 512, the apices 524, the eyelets 518 and/or portions of the tethers 520 by any of the above-described techniques. Further, the configuration may include a radiopaque portion 522 to aid in visualization during delivery. The radiopaque portion 520 may be disposed at selected apices 524, including all apices 524 if desired. The radiopaque portion 520 may be disposed underneath the graft material 516, as shown, or mark disposed on a portion of the second part 510 not covered by graft material 516. The radiopaque portion 520 may be in the form of a radiopaque marker.

Each of the embodiments described above may be implanted into a patient via any desired method, including, for example, through use of an insertion catheter. The device is first compressed to a smaller diameter, such as via rolling, and inserted into the catheter where it is held in the compressed state until implantation. The catheter is inserted into the patient's body lumen, and the implantable device is withdrawn from the catheter. The second part (i.e., the stent) is expanded, thus securing the device in the body lumen.

If desired, the implantable devices herein may include a second part at only one or at all open ends of the first part. For example, if the first part is a tubular graft, there may be a second part at both the proximal and the distal ends of the first part, using one or more of the attachment configurations described above. In addition, if the first part is a device including more than two open ends (i.e., a bifurcated or trifurcated device), any or all of the open ends may include an attachment flap and second part, using one or more of the attachment configurations described above. For example, the first open end of an implantable device may incorporate the attachment configuration of FIG. 2, while a second open end of an implantable device may incorporate the attachment configuration of FIG. 7. Any combination of attachment configurations described above may be used as desired.

The following embodiments or aspects of the invention may be combined in any fashion and combination and be within the scope of the present invention, as follows:

Embodiment 1. A device for implantation into a body lumen having a reduced implantation diameter, comprising:
(a) a generally tubular first part having a lumen extending therethrough for the flow of bodily fluid, said first part including a first open end and a second open end; and
(b) a second part attached to said first open end of said first part, wherein said second part is capable of securing said device into a body lumen;
wherein said first open end comprises an attachment flap that is compressible to a reduced diameter as compared to a device incorporating a full attachment ring, and wherein said attachment flap comprises a plurality of attachment sites secured by a plurality of attachment tethers.

Embodiment 2. The device of embodiment 1, wherein said second part is secured to said first part at said attachment sites.

Embodiment 3. The device of embodiment 1, wherein said attachment sites are secured to said attachment tethers through the use of FEP dispersion.

Embodiment 4. The device of embodiment 1, wherein said attachment sites are secured to said attachment tethers through heat compression, welding or sintering processes.

Embodiment 5. The device of embodiment 1, wherein said attachment tethers comprise PTFE, ePTFE, and combinations thereof.

Embodiment 6. The device of embodiment 1, wherein each of said attachment sites comprises an individual hole through said attachment flap.

Embodiment 7. The device of embodiment 1, wherein each of said attachment sites comprises physical interlocking of said second part and said tether.

Embodiment 8. The device of embodiment 1, wherein said attachment tethers are secured to said second part through eyelets in said second part.

Embodiment 9. The device of embodiment 8, wherein material from interior portions of the first part is folded over the eyelets in said second part.

Embodiment 10. A method of manufacturing a tubular prosthesis for delivery into a body lumen of a patient, comprising the steps of:
(a) providing a device for implantation into a body lumen having a reduced implantation diameter, comprising:
(i) a generally tubular first part having a lumen extending therethrough for the flow of bodily fluid, said first part including a first open end and a second open end; and (ii) a second part attached to said first open end of said first part, wherein said second part is capable of securing said device into a body lumen;
wherein said first open end comprises an attachment flap that is compressible to a reduced diameter as compared to a device incorporating a full attachment ring;
(b) providing a plurality of attachment sites comprising a plurality of tethers at said attachment flap for securing said first part and said second part to one and the other; and
(c) securing said first part and said second part to one and the other at said plurality of attachment sites.

Embodiment 11. The method of embodiment 10, wherein said second part is secured to said first part at said attachment sites.

Embodiment 12. The method of embodiment 10, wherein said attachment sites are secured to said attachment tethers through the use of FEP dispersion.

Embodiment 13. The method of embodiment 10, wherein said attachment tethers comprise PTFE, ePTFE, and combinations thereof.

Embodiment 14. The method of embodiment 10, wherein each of said attachment sites comprises an individual hole through said attachment flap.

Embodiment 15. The method of embodiment 10, wherein each of said attachment sites comprises physical interlocking of said second part and said tether.

Embodiment 16. The method of embodiment 10, wherein said attachment tethers are secured to said second part through eyelets in said second part.

Embodiment 17. The method of embodiment 10, wherein material from interior portions of the first part is folded over the eyelets in said second part.

Embodiment 18. A method of implanting a tubular prosthesis into a body lumen of a patient, comprising the steps of:
(a) providing a device for implantation into a body lumen having a reduced implantation diameter, comprising:
(i) a generally tubular first part having a lumen extending therethrough for the flow of bodily fluid, said first part including a first open end and a second open end; and
(ii) a second part attached to said first open end of said first part, wherein said second part is capable of securing said device into a body lumen;
wherein said first open end comprises an attachment flap that is compressible to a reduced diameter as compared to a device incorporating a full attachment ring, and wherein said attachment flap comprises a plurality of attachment sites secured by a plurality of attachment tethers; and
(b) delivering the device to a desired location within the body lumen.

The various embodiments described herein are useful in allowing for the implantation of prosthetic devices into relatively narrow spaces (i.e., body lumens) in a safer and more secure fashion. Allowing for the compression of such devices to reduce the diameter of the device during implantation is an important and effective means to safely implanting such devices into patients' bodies.

While various embodiments of the present invention are specifically illustrated and/or described herein, it will be appreciated that modifications and variations of the present invention may be effected by those skilled in the art without departing from the spirit and intended scope of the invention. For example, the reinforced holes and/or eyelets may have any suitable configuration for receiving attachment members and/or tethers, including without limitation the size and configuration of holes or orifices of the reinforced holes and/or eyelets through which the attachment members and/or tethers are disposed. Further, the shapes and sizes of the attachment members and/or tethers may be varied. Moreover, modifications of reinforcement tabs and/or graft materials for providing reinforcement, including weld lines, are within the scope of the present invention. Still further, any of the embodiments or aspects of the invention as described in the claims or in the specification may be used with one and another without limitation.

What is claimed is:

1. A device for implantation into a body lumen having a low profile implantation diameter, comprising:
an expandable stent member having apices at at least one end with an eyelet disposed at each of the apices, wherein said stent member is capable of securing said device into a body lumen;
a plurality of attachment tethers looped through each of the eyelets;
a generally tubular graft having a lumen extending therethrough for the flow of bodily fluid, said graft comprising a first open end, a second open end, and a graft wall having an interior surface and an opposed exterior surface, said graft wall comprising a plurality of layers with internal layers disposed between the interior surface and the opposed exterior surface; wherein the eyelets, the apices having the eyelets and the plurality of attachment tethers are disposed over a portion of the exterior surface of the graft near the first open end of the graft; and
an attachment flap;
wherein material from at least one of the internal layers forming the graft wall is extended and folded over at said first end to define said attachment flap which covers the eyelets, covers the apices having the eyelets and covers at least a portion of the plurality of attachment tethers; and
wherein the attachment flap is secured over the portion of the exterior surface of the graft near the first open end and over the at least portion of the plurality of attachment tethers to define a plurality of attachment sites thereat.

2. The device of claim 1, wherein said attachment flap is secured to said attachment tethers and to said portion of the exterior surface of the graft through the use of FEP dispersion.

3. The device of claim 1, wherein said attachment flap is secured to said attachment tethers and to said portion of the exterior surface of the graft through heat compression, welding or sintering processes.

4. The device of claim 1, wherein said attachment tethers comprise PTFE, ePTFE, and combinations thereof.

5. A method of manufacturing a tubular prosthesis for delivery into a body lumen of a patient, comprising the steps of:
providing a device for implantation into a body lumen having a low profile implantation diameter, comprising:
an expandable stent member having apices at at least one end with an eyelet disposed at each of the apices, wherein said stent member is capable of securing said device into a body lumen;
a plurality of attachment tethers looped through of the eyelets;
a generally tubular graft having a lumen extending therethrough for the flow of bodily fluid, said graft comprising a first open end, a second open end, and a graft wall having an interior surface and an opposed exterior surface, said graft wall comprising a plurality of layers with internal layers disposed between the interior surface and the opposed exterior surface; wherein the eyelets, the apices having the eyelets and the plurality of attachment tethers are disposed over a portion of the exterior surface of the graft near the first open end of the graft; and wherein said first open end of the graft comprises an attachment flap;

wherein material from at least one of the internal layers forming the graft wall is extended and folded over at said first end to define said attachment flap which covers the eyelets, covers the apices having the eyelets and covers at least a portion of the plurality of attachment tethers;

disposing the eyelets, the apices having the eyelets and the plurality of attachment tethers over a portion of the exterior surface of the graft near the first open end of the graft; and securing said attachment flap over the portion of the exterior surface of the graft near the first open end and over the at least portion of plurality of attachment tethers to define a plurality of attachment sites.

6. The method of claim 5, wherein said attachment flap is secured to said attachment tethers and to said portion of the exterior surface of the graft through the use of FEP dispersion.

7. The method of claim 5, wherein said attachment tethers comprise PTFE, ePTFE, and combinations thereof.

8. A method of implanting a tubular prosthesis into a body lumen of a patient, comprising the steps of:
(a) providing a device for implantation into a body lumen having a low profile implantation diameter, comprising:
an expandable stent member having apices at at least one end with an eyelet disposed at each of the apices, wherein said stent member is capable of securing said device into a body lumen;
a plurality of attachment tethers looped through each of the eyelets;
a generally tubular graft having a lumen extending therethrough for the flow of bodily fluid, said graft comprising a first open end, a second open end, and a graft wall having an interior surface and an opposed exterior surface, said graft wall comprising a plurality of layers; wherein the eyelets, the apices having the eyelets and the plurality of attachment tethers are disposed over a portion of the exterior surface of the graft near the first open end of the graft; and
an attachment flap;
wherein material from at least one of the internal layers forming the graft wall is extended and folded over at said first end to define said attachment flap which covers the eyelets, covers the apices having the eyelet and covers at least a portion of the plurality of attachment tethers; and
wherein the attachment flap is secured over the portion of the exterior surface of the graft near the first open end and over the at least portion of the plurality of attachment tethers to define a plurality of attachment sites thereat; and
(b) delivering the device to a desired location within the body lumen.

* * * * *